(12) United States Patent
Al-khalidy et al.

(10) Patent No.: US 7,046,759 B2
(45) Date of Patent: May 16, 2006

(54) METHOD AND SYSTEM FOR IMAGING A VOLUME USING A THREE-DIMENSIONAL SPIRAL SCAN TRAJECTORY

(75) Inventors: Abdulrahman Al-khalidy, Clifton Park, NY (US); Jeffrey Wayne Eberhard, Albany, NY (US); Abdalmajeid Alyassin, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 201 days.

(21) Appl. No.: 10/813,100

(22) Filed: Mar. 30, 2004

(65) Prior Publication Data

US 2005/0226370 A1 Oct. 13, 2005

(51) Int. Cl.
*A61B 6/03* (2006.01)

(52) U.S. Cl. .............. 378/22; 378/15; 378/901
(58) Field of Classification Search ............ 378/4, 378/15, 20, 22, 901
See application file for complete search history.

(56) References Cited

U.S. PATENT DOCUMENTS

2005/0265514 A1* 12/2005 Sugihara et al. .............. 378/15

OTHER PUBLICATIONS

Eberhard et al, "Method and System for Three Dimensional Tomosynthesis Imaging," U.S. Appl. 10/739,541, filed Dec. 18, 2003.
J.T. Dobbins, et al, "Tomosynthesis for improved pulmonary nodule detection", RSNA abstract No. 605, Vol. 290, pp. 280, 1998.
K.R. Maravilla, et al, "Digital Tomosynthesis: Technique for Electronic Reconstructive Tomography", AJNR:4, pp.: 883-888, 1983.

* cited by examiner

*Primary Examiner*—David V Bruce
(74) *Attorney, Agent, or Firm*—Fletcher Yoder

(57) ABSTRACT

A technique is provided for improving the depth resolution of tomosynthesis images. The technique provides for the use of spiral scan trajectories. The X-ray source may moved along the spiral scan trajectory, acquiring projection data at various locations on the trajectory which are offset in the z-direction, i.e., in a direction perpendicular to the detector. Projection data acquired at different positions in the z-direction may be used to generate three-dimensional, tomosynthesis images having improved depth resolution.

20 Claims, 4 Drawing Sheets

METHOD AND SYSTEM FOR IMAGING A VOLUME USING A THREE-DIMENSIONAL SPIRAL SCAN TRAJECTORY

BACKGROUND OF THE INVENTION

The present invention relates generally to the field of medical imaging, and more specifically to the field of tomosynthesis. In particular, the present invention relates to the use of three-dimensional scan trajectories during acquisition of image data.

Tomosynthesis is an imaging modality that may be used, in a medical context, to allow physicians and radiologists to non-invasively obtain three-dimensional representations of selected organs or tissues of a patient. In tomosynthesis, projection radiographs, conventionally known as X-ray images, are acquired at different angles relative to the patient. Typically, a limited number of projection radiographs are acquired over a relatively small angular range. The projections comprising the radiographs generally represent the line integrals of the attenuation coefficients along the respective X-ray paths through the patient and, therefore, convey useful data regarding internal structures.

From the acquired projection radiographs, a three-dimensional representation of the imaged volume may be reconstructed. Typically, the reconstructed data set may be arranged in planar cross-sections, i.e., slices, of the volume at different heights, each slice being parallel to the plane of the X-ray detector. The reconstructed data set may be reviewed by a technologist or radiologist trained to generate a diagnosis or evaluation based on such data. In such a medical context, tomosynthesis may provide three-dimensional shape and location information of structures of interest as well as an increased conspicuity of the structures within the imaged volume.

The quality of the three-dimensional rendering available for viewing may depend, in large part, on the quality of the acquired projection data. For objects that are small relative to the size of the detector, the quality of the projection data, in turn, is generally limited by the range of angles over which the projection data is acquired. Therefore, the quality of the acquired projections typically depends, at least in part, on the scan trajectory traveled by the X-ray source during acquisition of the projection image data.

One-dimensional, i.e., linear scan trajectories, and two-dimensional, i.e., planar, scan trajectories yield a specific depth resolution, i.e., the resolution in the direction perpendicular to the detector surface, which is reflected in the subsequent three-dimensional rendering. In particular, for one-dimensional and two-dimensional scan trajectories, the depth information is defined by the scanning angles and is specific to each trajectory. Because depth resolution is limited by the available range of motion of the X-ray source, the depth resolution may not be as good as the resolution in the plane parallel to the detector surface. A technique for acquiring projection images during tomosynthesis that provides improved depth resolution may, therefore, be desirable.

BRIEF DESCRIPTION OF THE INVENTION

The present technique provides a novel approach to acquiring projection images during tomosynthesis. In particular, the present technique provides for the use of three-dimensional scan trajectories for use in the acquisition of tomosynthesis projection images. The depth resolution of three-dimensional images reconstructed from projection images acquired at different locations along the z-axis may be improved relative to similar images derived from projection data acquired using one and two-dimensional scan trajectories.

In accordance with one aspect of the technique, a method is provided for generating a three-dimensional image. In accordance with the aspect, an X-ray source is moved along a three-dimensional trajectory. Projection data may be acquired at a plurality of locations on the three-dimensional trajectory. Projection data generated from different heights relative to a detector surface may convey greater depth information than projection data acquired along a two-dimensional trajectory. A three-dimensional may be generated from the projection data. Systems and computer programs that afford functionality of the type defined by these aspects are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

In the field of medical imaging, various imaging modalities may be employed to non-invasively examine and/or diagnose internal structures of a patient using various physical properties. One such modality is tomosynthesis imaging which utilizes a limited number of projection radiographs that are each acquired at a different angle relative to a patient. The projection radiographs may be combined to generate a set of data that provides three-dimensional context and structure for the volume of interest. Typically, the projection radiographs are generated using an X-ray source moving in a plane parallel to a detector. The X-ray source may move in one or two dimensions within the plane. The linear and/or planar movement of the X-ray source effectively limits the depth resolution that may be achieved in three-dimensional images reconstructed from the acquired projection data. The present technique is directed to the improvement of depth resolution by incorporating motion along the depth dimension into the scan trajectory traveled by the X-ray source.

Figure 1:
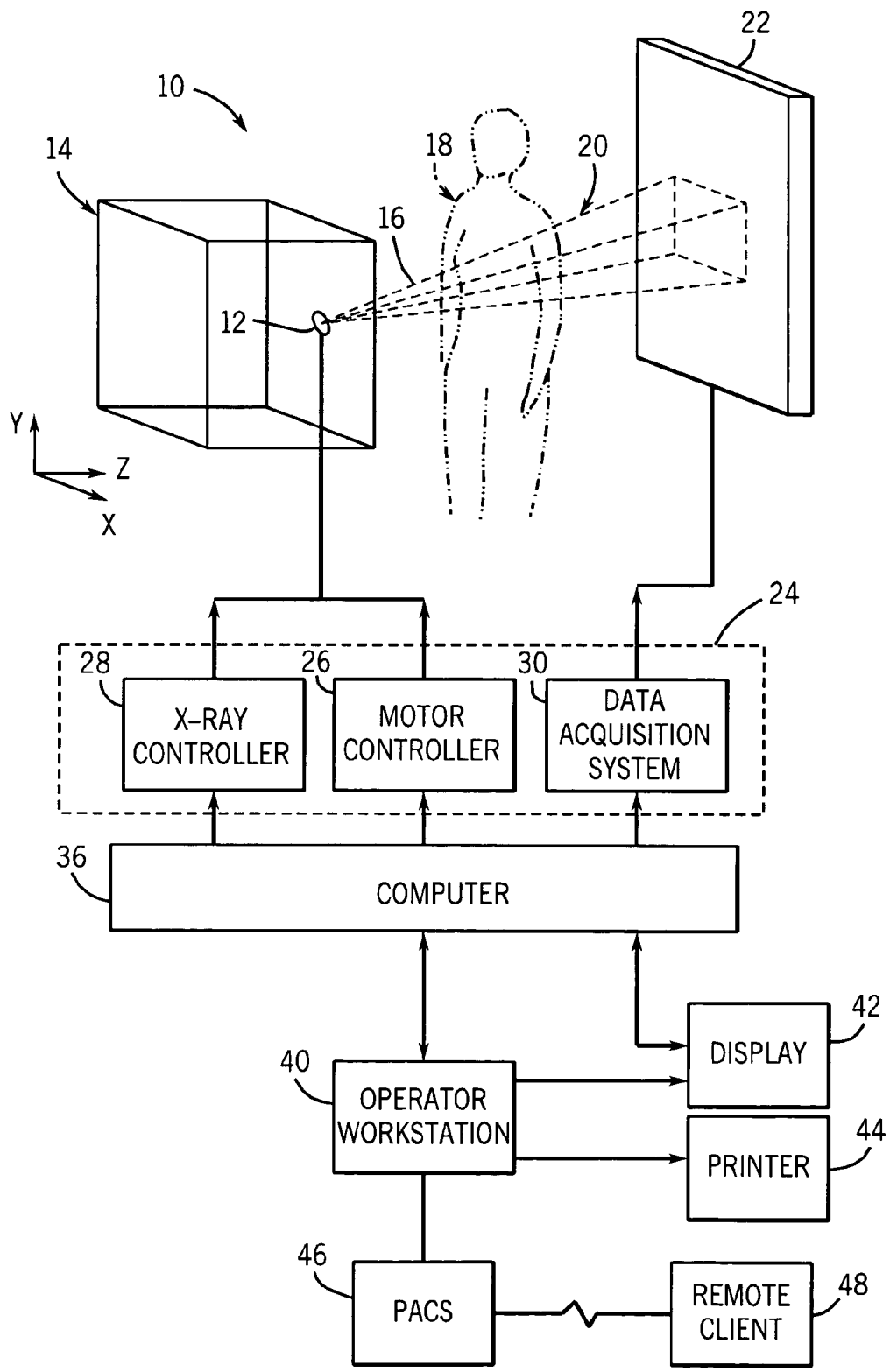
FIG. 1 is a diagrammatical view of an exemplary imaging system in the form of a tomosynthesis imaging system for use in producing processed images, in accordance with aspects of the present technique.

An example of a tomosynthesis imaging system 10 capable of acquiring and/or processing image data in accordance with the present technique is illustrated diagrammatically in FIG. 1. As depicted, the tomosynthesis imaging system 10 includes an X-ray source 12, such as an X-ray tube, and associated support and filtering components. The X-ray source 12 may be moved within a constrained region. As one of ordinary skill in the art will appreciate, the constrained region may be arcuate or otherwise three-dimensional. For simplicity, the constrained region is depicted and discussed herein as a cubic volume 14 within which the source 12 may move in three-dimensions, depicted in FIG. 1 as x and y dimensions, corresponding to the surface of a detector array 22, and a z dimension which is orthogonal to the x,y-plane.

A stream of radiation 16 is emitted by the source 12 and passes into a region in which a subject, such as a human patient 18, is positioned. A portion of the radiation 20 passes through or around the subject and impacts the detector array, represented generally at reference numeral 22. The detector 22 is generally formed by a plurality of detector elements, generally corresponding to pixels, which produce electrical signals that represent the intensity of the incident X-rays. These signals are acquired and processed to reconstruct an image of the features within the subject. A collimator may also be present, which defines the size and shape of the X-ray beam 16 that emerges from the X-ray source 12.

Source 12 is controlled by a system controller 24 which furnishes both power and control signals for tomosynthesis examination sequences. Moreover, detector 22 is coupled to the system controller 24, which commands acquisition of the signals generated by the detector 22. The system controller 24 may also execute various signal processing and filtration functions, such as for initial adjustment of dynamic ranges, interleaving of digital image data, and so forth. In general, the system controller 24 commands operation of the imaging system 10 to execute examination protocols and to acquire the resulting data.

In the exemplary imaging system 10, the system controller 24 commands the movement of the source 12 within the volume 14 via a motor controller 26, which moves the source 12 relative to the patient 18 and the detector 22. In alternative implementations, the motor controller 26 may move the detector 22, or even the patient 18, instead of or in addition to the source 12. Additionally, the system controller 24 may include an X-ray controller 28 to control the activation and operation of the X-ray source 12. In particular, the X-ray controller 28 may be configured to provide power and timing signals to the X-ray source 12. By means of the motor controller 26 and X-ray controller 28, the system controller 24 may facilitate the acquisition of radiographic projections at various angles through the patient 18.

The system controller 24 may also include a data acquisition system 30 in communication with the detector 22. The data acquisition system 30 typically receives data collected by readout electronics of the detector 22, such as sampled analog signals. The data acquisition system 30 may convert the data to digital signals suitable for processing by a processor-based system, such as a computer 36.

The computer 36 is typically coupled to the system controller 24. The data collected by the data acquisition system 30 may be transmitted to the computer 36 for subsequent processing and reconstruction. For example, the data collected from the detector 22 may undergo pre-processing and calibration at the data acquisition system 30 and/or the computer 36 to condition the data to represent the line integrals of the attenuation coefficients of the scanned objects. The processed data, commonly called projections, may then be backprojected to formulate an image of the scanned area. Once reconstructed, the images produced by the system of FIG. 1 reveal an internal region of interest of the patient 18 which may be used for diagnosis, evaluation, and so forth.

The computer 36 may comprise or communicate with memory circuitry that can store data processed by the computer 36 or data to be processed by the computer 36. It should be understood that any type of computer accessible memory device capable of storing the desired amount of data and/or code may be utilized by such an exemplary system 10. Moreover, the memory circuitry may comprise one or more memory devices, such as magnetic or optical devices, of similar or different types, which may be local and/or remote to the system 10. The memory circuitry may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe reconstructed images and other data relevant to the system 10 from computer 36, initiate imaging, and so forth.

A display 42 coupled to the operator workstation 40 may be utilized to observe the reconstructed images and to control imaging. Additionally, the images may also be printed by a printer 44 that may be coupled to the operator workstation 40. The display 42 and printer 44 may also be connected to the computer 36, either directly or via the operator workstation 40. Further, the operator workstation 40 may also be coupled to a picture archiving and communications system (PACS) 44. It should be noted that PACS 44 may be coupled to a remote system 46, radiology department information system (RIS), hospital information system (HIS) or to an internal or external network, so that others at different locations may gain access to the image and to the image data.

It should be further noted that the computer 36 and operator workstation 40 may be coupled to other output devices that may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Once reconstructed and combined, the image data generated by the system of FIG. 1 reveals the three-dimensional relationship of internal features of the patient 18. The reconstructed three-dimensional image, however, may have an associated depth resolution, i.e., resolution in the z-dimension, that is less than that associated with the x,y-plane, which is generally a function of the properties of the detector array 22. In particular, the associated depth resolution may be unsuitable for the desired use or may otherwise detract from the accurate perception of depth in the three-dimensional image.

The depth resolution of the three-dimensional image, as noted above, may largely be a function of the scan trajectory traveled by the X-ray source 12 during acquisition of the projection images. In particular, one-dimensional and two-dimensional scan trajectories, i.e., trajectories limited to the x,y-plane, may provide insufficient information to achieve higher depth resolutions. One possibility, therefore, is to utilize three-dimensional scan trajectories, herein referred to as spiral scan trajectories, during projection acquisition. Such a spiral scan trajectory would allow projection images of a region of interest to be acquired from different distances, thereby achieving different perspectives and potentially greater depth information. Three-dimensional images reconstructed from projections acquired along a spiral scan trajectory may, therefore, improve depth resolution in the resulting volume renderings.

In particular, the depth resolution, as well as the in-plane resolution, of a region is affected by how the region is sampled in three-dimensions, i.e., by the spiral scan trajectory. Therefore, scan trajectories defined by only one or two dimensions, i.e., constant in the z-dimension, do not provide as much flexibility in obtaining the desired depth resolution as those which utilize all three dimensions.

Furthermore, since X-ray intensity changes with the inverse squared distance from the X-ray source 12, spiral scan trajectories may provide a mechanism for dose management during the tomosynthesis imaging process. In particular, the motion of the source 12 in three dimensions provides greater flexibility in controlling the X-ray dose received by a patient 18 at any particular location. For example, a spiral scan trajectory may be configured or selected which provides relatively lower dosage to the region of interest while also maximizing the depth information obtained of the region of interest or the surrounding area. Similarly, the operation of the source 12 may be varied based upon the position of the source 12 on the spiral scan trajectory. For example, intensity, spectrum or collimation of the X-ray source 12 may be varied based on the position of the X-ray source 12, the generator power, and/or the collimator capabilities.

Selection of a spiral scan trajectory may be based on various factors, including customization based on region of interest, desired dose, desired X-ray intensity, and so forth. Though the term spiral scan trajectory is used herein, it is to be understood that the actual trajectory traced by the X-ray source may be any three-dimensional scan trajectory, including arbitrary three-dimensional scan trajectories. The term spiral scan trajectory, therefore, encompasses not only spiral motion but also other curved and circular motion as well as linear and arbitrary motion.

Furthermore, a spiral scan trajectory may be based on a one or two dimensional scan trajectory with certain desirable characteristics. For example, a two-dimensional scan trajectory that achieves desirable results, such as improved data completeness, may be modified and further enhanced by adding a z-direction component to generate a suitable spiral scan trajectory. The distance traveled by the source 12 in the z-direction may vary depending on the application, desired scan trajectory, the region of interest, and/or patient specific factors. The motion of the X-ray source 12 may be continuous, such that the X-ray source 12 remains in motion along the spiral scan trajectory, though the velocity of the X-ray source 12 may vary or may be constant along the spiral scan trajectory. Alternatively, the motion of the X-ray source 12 may be discontinuous, such that the X-ray source 12 intermittently stops at different points on the spiral scan trajectory, such as during the emission of X-rays.

Figure 2:
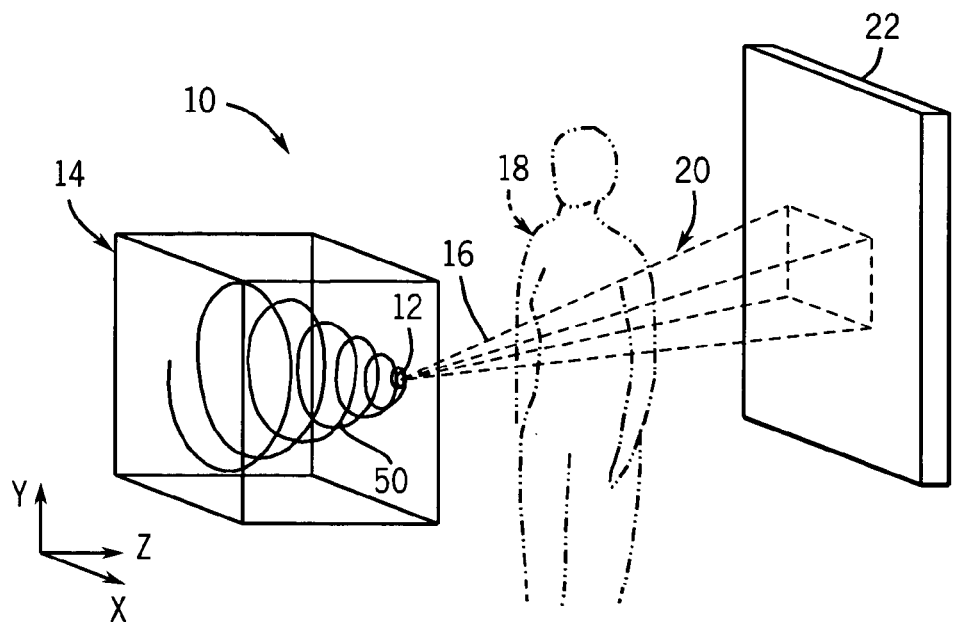
FIG. 2 depicts a spiral three-dimensional scan trajectory for use in tomosynthesis, in accordance with aspects of the present technique.
Figure 3:
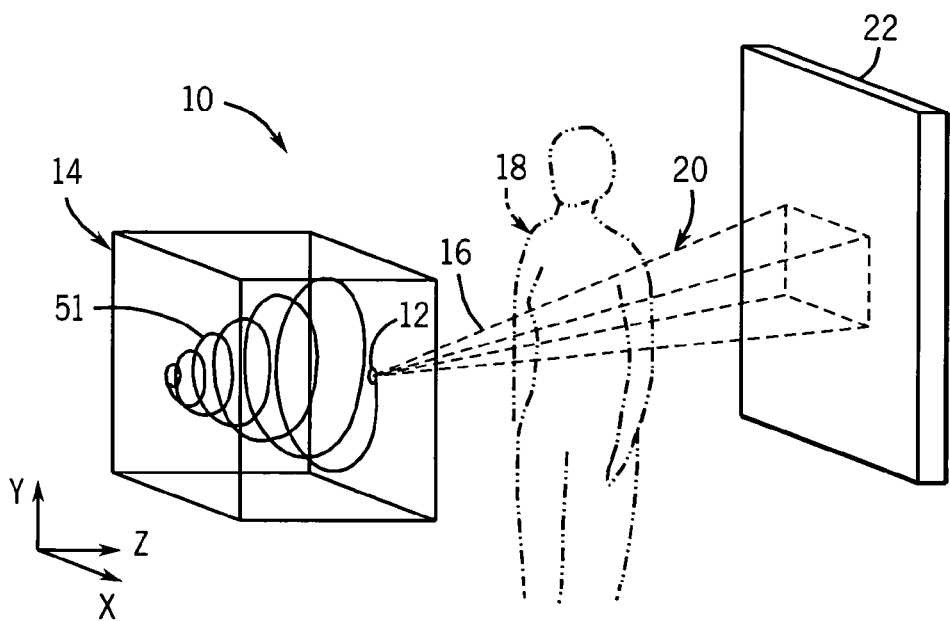
FIG. 3 depicts another spiral three-dimensional scan trajectory for use in tomosynthesis, in accordance with aspects of the present technique.

For example, FIGS. 2–7 depict possible scan trajectories that may produce desirable depth resolutions. FIG. 2, for example, depicts a first spiral trajectory 50 based on spiral motion that originates from the point closest to the patient 18 and unwinds in a spiral pattern (in the x,y-plane) as the source 12 moves away from the patient 18 in the z-direction. Conversely, FIG. 3 depicts a second spiral trajectory 51 based on a spiral motion that originates at the point farthest from the patient 18 and unwinds in a spiral pattern as the source 12 moves toward the patient 18 in the z-direction.

Figure 4:
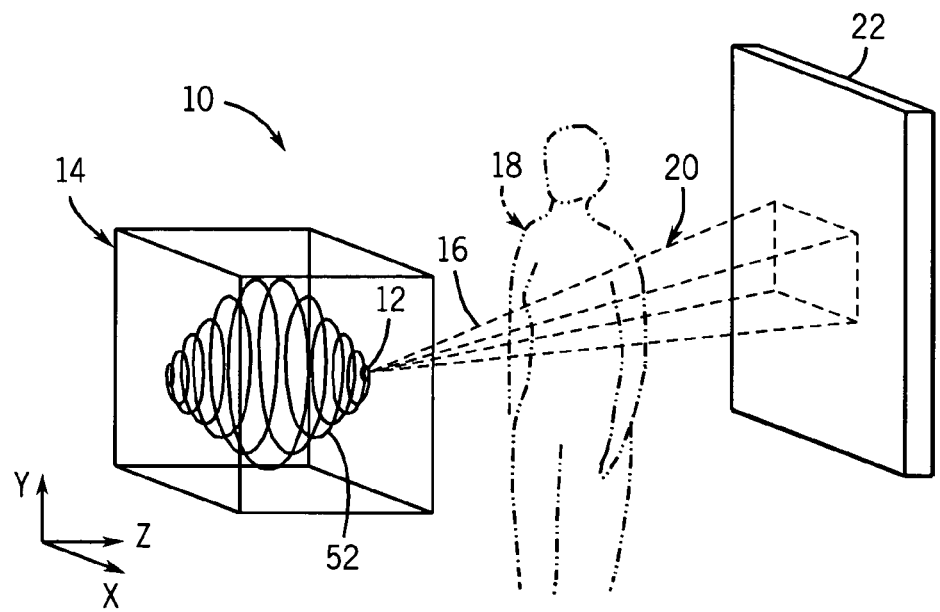
FIG. 4 depicts a composite spiral three-dimensional scan trajectory for use in tomosynthesis, in accordance with aspects of the present technique.
Figure 5:
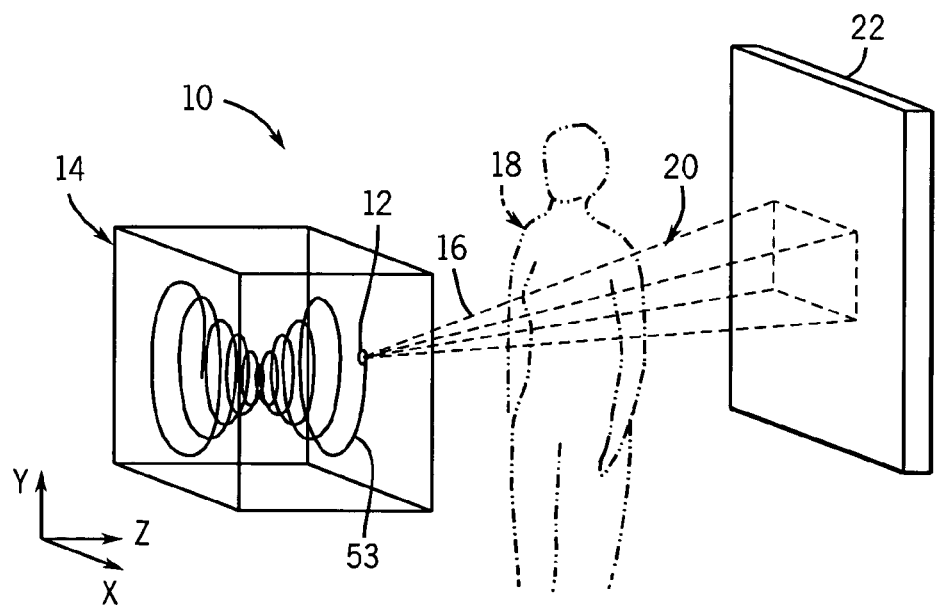
FIG. 5 depicts another composite spiral three-dimensional scan trajectory for use in tomosynthesis, in accordance with aspects of the present technique.
Figure 6:
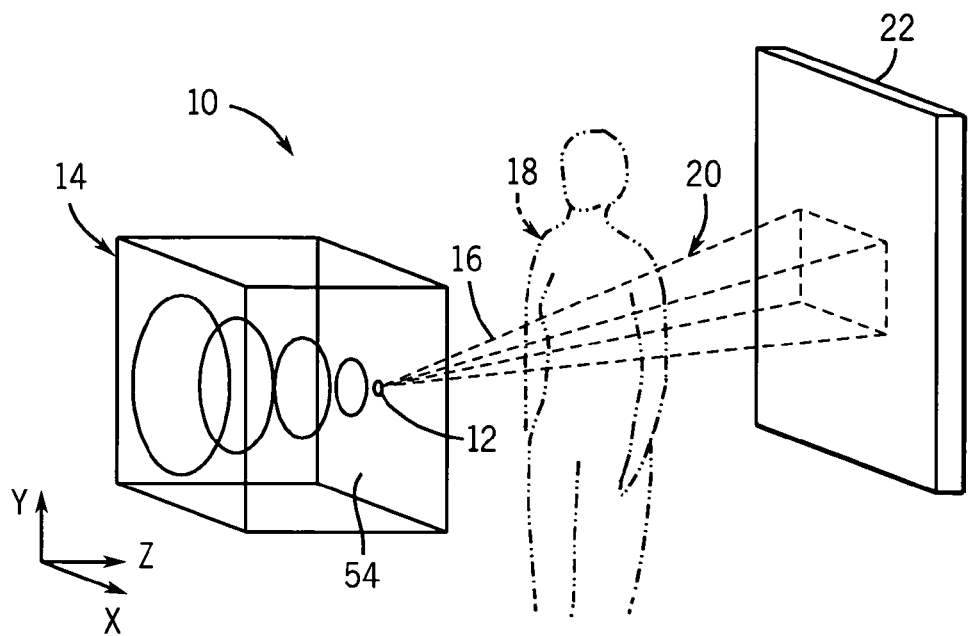
FIG. 6 depicts a step-and-shoot three-dimensional scan trajectory for use in tomosynthesis, in accordance with aspects of the present technique.

The spiral trajectories 50, 51 depicted in FIGS. 2 and 3 may be combined, as depicted in FIG. 4, to generate a first composite trajectory 52 that originates at the point farthest from the patient 18 and unwinds as the source 12 moves toward the patient 18 in the z-direction. At a central point, however, the source 12 winds inward as the source 12 moves to the point closest to the patient 18 in the z-direction. Alternately, as one of ordinary skill in the art will appreciate, the spiral trajectories 50, 51 may be combined in an alternate fashion to yield a second composite trajectory 53, as depicted in FIG. 5, that originates at the point farthest from the patient 18 and winds inward as the source 12 moves toward the patient 18 in the z-direction. At a central point, however, the source 12 unwinds as the source 12 moves to the point closest to the patient 18 in the z-direction. The spiral and composite trajectories 50, 51, 52, 53 described herein may possess various desirable attributes. For example, such trajectories may minimize data incompleteness, thereby improving image quality. In addition to these benefits, the z-direction component to the trajectories allows for better depth resolution in the three-dimensional images derived from projection data acquired at intervals along such spiral and composite trajectories 50, 51, 52, 53.

While scan trajectories incorporating spiral motion represent one possibility, other three-dimensional scan trajectories are also possible. For example, multi-planar trajectories 54 may be desirable in some circumstances. Such multi-planar trajectories 54 may involve moving the X-ray source during acquisition in a two-dimensional at a first distance in the z-direction from the patient 18. The source 12 may then be moved toward or away from the patient 18 to a new location on the z-axis, where the source 12 is moved in a two-dimensional profile during acquisition at the new z-location. For example, referring to FIG. 6, the two-dimensional profile depicted is a circle that increases in radius as the distance from the patient 18 to the source 12 increases. As one of ordinary skill in the art will appreciate, the shape of the two-dimensional profile may change or remain the same at different planes of the multi-planar trajectory 54. Likewise, the size of the two-dimensional profile may change or remain the same at different planes of the multi-planar trajectory 54.

Figure 7:
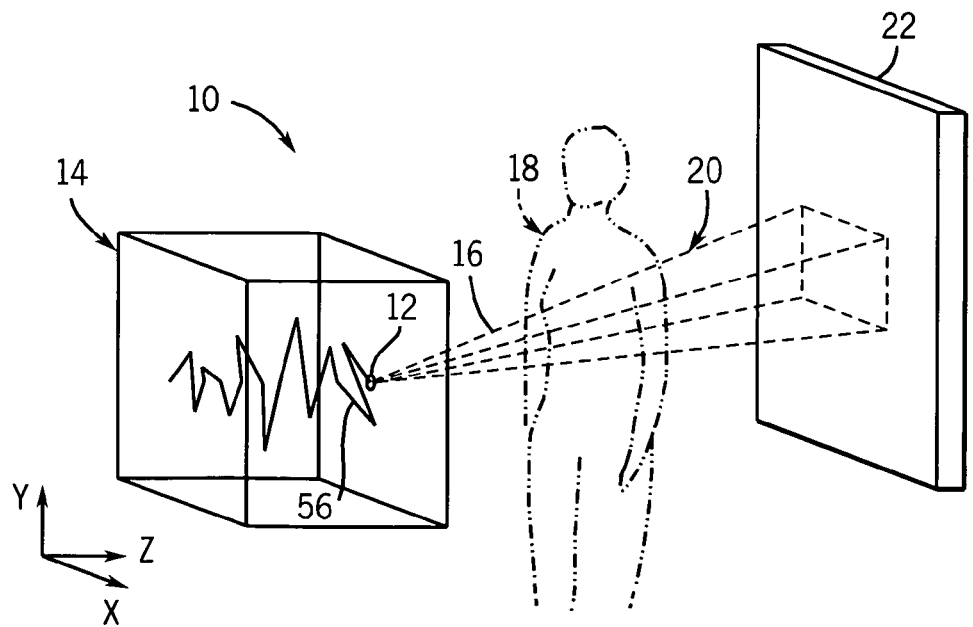
FIG. 7 depicts an arbitrary three-dimensional scan trajectory for use in tomosynthesis, in accordance with aspects of the present technique.

While FIGS. 2–6 depict three-dimensional trajectories having a geometric or symmetric regularity, the three-dimensional trajectory may instead be essentially arbitrary in character, based on the application or other considerations. For example, the three-dimensional trajectory may be an arbitrary trajectory 56, such as a zig-zag trajectory, as depicted in FIG. 7. Such an arbitrary trajectory 56 may range over the full height of the detector 22 but only a portion of the width of the detector 22, the full width of the detector 22 and a multiple of the height of the detector 22, or the full height of the detector 22 and a multiple of the width of the detector 22. Other arbitrary trajectories are of course possible, however, based on the demands of the application and/or the patient. As one of ordinary skill in the art will readily appreciate, the preceding examples are merely illustrative of the present techniques. Other three-dimensional scan trajectories than those discussed herein may be employed which result in improvement of depth resolution of the resulting three-dimensional images. The present technique, therefore, encompasses other three-dimensional trajectories providing improvement in depth resolution, not merely those discussed herein.

The invention may be susceptible to various modifications and alternative forms, and specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating a three-dimensional image, comprising:
    moving an X-ray source along a spiral scan trajectory;
    acquiring projection data at a plurality of locations on the spiral scan trajectory, wherein projection data generated from different heights relative to a detector surface conveys greater depth information than projection data acquired along a two-dimensional trajectory; and
    generating a three-dimensional image from the projection data.

2. The method, as recited in claim 1, wherein the X-ray source is configured to move continuously along the spiral scan trajectory.

3. The method, as recited in claim 1, wherein the X-ray source is configured to move discontinuously along the spiral scan trajectory.

4. The method, as recited in claim 1, wherein the spiral scan trajectory comprises one of a spiral trajectory, a composite trajectory, a multi-planar-trajectory, and an arbitrary trajectory.

5. The method, as recited in claim 1, comprising:
    selecting the spiral scan trajectory based on a desired dosage for a region of interest.

6. The method, as recited in claim 1, comprising:
    adjusting an operating characteristic of the X-ray source based on the location on the spiral scan trajectory.

7. The method, as recited in claim 1, comprising:
    selecting a spiral scan trajectory based upon a two-dimensional trajectory having one or more desired characteristics.

8. A computer program, provided on one or more computer readable media, for generating a three-dimensional image, comprising:
    a routine for moving an X-ray source along a spiral scan trajectory;
    a routine for acquiring projection data at a plurality of locations on the spiral scan trajectory, wherein projection data generated from different heights relative to a detector surface conveys greater depth information than projection data acquired along a two-dimensional trajectory; and
    a routine for generating a three-dimensional image from the projection data.

9. The computer program, as recited in claim 8, wherein the routine for moving the X-ray source moves the X-ray source continuously along the spiral scan trajectory.

10. The computer program, as recited in claim 8, wherein the routine for moving the X-ray source moves the X-ray source discontinuously along the spiral scan trajectory.

11. The computer program, as recited in claim 8, wherein the spiral scan trajectory comprises one of a spiral trajectory, a composite trajectory, a multi-planar-trajectory, and an arbitrary trajectory.

12. The computer program, as recited in claim 8, comprising:
    a routine for selecting the spiral scan trajectory based on a desired dosage for a region of interest.

13. The computer program, as recited in claim 8, comprising:
    a routine for adjusting an operating characteristic of the X-ray source based on the location on the spiral scan trajectory.

14. The computer program, as recited in claim 8, comprising:
    a routine for selecting a spiral scan trajectory based upon a two-dimensional trajectory having one or more desired characteristics.

15. A tomosynthesis imaging system, comprising:
    means for moving an X-ray source along a spiral scan trajectory;
    means for acquiring projection data at a plurality of locations on the spiral scan trajectory, wherein projection data generated from different heights relative to a detector surface conveys greater depth information than projection data acquired along two-dimensional trajectory; and
    means for generating a three-dimensional image from the projection data.

16. A tomosynthesis imaging system, comprising:
    an X-ray source configured to emit a stream of radiation through a volume of interest at a plurality of locations along a spiral scan trajectory;
    a detector array comprising a plurality of detector elements, wherein each detector element may generate one or more signals in response to the respective streams of radiation and wherein the one or more signals generated in response to streams of radiation emitted at different heights relative to the detector convey greater depth information than projection data acquired along a two-dimensional trajectory;
    a system controller configured to control the X-ray source and to acquire the one or more signals from the plurality of detector elements;
    a computer system configured to receive the one or more signals and to generate a three-dimensional image from the one or more signals; and
    an operator workstation configured to display the rendered image.

17. The tomosynthesis imaging system, as recited in claim 16, wherein the X-ray source is configured to move continuously along the spiral scan trajectory.

18. The tomosynthesis imaging system, as recited in claim 16, wherein the X-ray source is configured to move discontinuously along the spiral scan trajectory.

19. The tomosynthesis imaging system, as recited in claim 16, wherein the spiral scan trajectory comprises one of a spiral trajectory, a composite trajectory, a multi-planar-trajectory, and an arbitrary trajectory.

20. The tomosynthesis imaging system, as recited in claim 16, wherein an operating characteristic of the X-ray source is adjusted based on the location of the X-ray source on the spiral scan trajectory.

* * * * *